United States Patent [19]

Bretaudiere et al.

[11] 4,279,862
[45] Jul. 21, 1981

[54] CENTRIFUGAL PHOTOMETRIC ANALYZER

[76] Inventors: Jean-Pierre Bretaudiere, 1 Alden Pl., Schenectady, N.Y. 12308; Paul Prunenec, 44, Rue des Ecoles, Paris, France, 75005

[21] Appl. No.: 961,478

[22] Filed: Nov. 16, 1978

[30] Foreign Application Priority Data

Nov. 17, 1977 [FR] France .................................. 77 34544

[51] Int. Cl.³ ............................................ G01N 21/07
[52] U.S. Cl. ...................................... 422/72; 233/26; 356/246
[58] Field of Search ............... 422/72; 356/39, 197 R, 356/246; 250/576; 233/26

[56] References Cited

U.S. PATENT DOCUMENTS

| 3,795,451 | 3/1974 | Mailen | 422/72 |
| 3,829,223 | 8/1974 | Hammel | 422/72 |
| 4,154,793 | 5/1979 | Gaigan | 422/72 |

FOREIGN PATENT DOCUMENTS 1432428  4/1976  United Kingdom ..................... 422/72

*Primary Examiner*—Michael Marcus
*Attorney, Agent, or Firm*—Darby & Darby

[57] ABSTRACT

A centrifugal analyzer which includes a rotating disc having a pair of wells, one for the reagent and another of the sample, which are connected to a measuring chamber by a transfer channel which has means for creating a pressure differential and/or turbulence to produce a homogeneous mixture.

13 Claims, 3 Drawing Figures

CENTRIFUGAL PHOTOMETRIC ANALYZER

The present invention relates to an improvement in devices for analysis by centrifugation.

A centrifugal photometric analyzer of the type in which a disc is equipped with series of loading wells and measuring curet, or chamber, is described in Fr. Pat. No. 73-35,745. Although the analyzers built according to the said French Patent are satisfactory, further improvements are desirable if a large number of measurements are to be made in a very short time after the disc is set in rotation. As a matter of fact, the discs used at present do not make it possible to obtain a homogeneous mixture in a very short time by the action of centrifugal force alone. Therefore, it is necessary to employ techniques such as, for example, acceleration-braking-acceleration, or creation of a partial vacuum at the perimeter or at the center of the disc, etc. As a result, it is not possible, with this type of disc and analyzer, to make large number of measurements in a time of less than a second, on a homogenous reaction mixture. This becomes increasingly so in the case where the discs are solid with a disc holder which thereby increases the inertia when rotation is started. Furthermore, if a large number of measurements are to be made in very short intervals of time, it is necessary to make use of an electronic computer having sophisticated performance characteristics which are disproportionate with the object to be achieved. Also, the discs in use at present are specialized in the sense that they do not permit the use of different analysis principles in the course of a single rotation, for example, spectrophotometry and spectrofluorometry.

The object of the invention is to avoid the above-mentioned drawbacks by obtaining in a very brief time a homogeneous mixture of the reagent and the sample, with the use of just centrifugal force. Also, a large number of measurements are made at very short intervals of time, starting shortly after the reaction mixture is placed in the reading chamber. The invention also uses no disc holder, in order to diminish the inertia when rotation is started. Further, by varying the angle of incidence of the electromagnetic radiation during the course of analysis, an analyses based on different measurement principles is made in the course of a single rotation. The device of the invention also can measure the signals from the measuring cuvette at their peak value corresponding to the center of the said cuvette and store them in an auxliary memory for subsequent processing by an electronic computer.

Accordingly, the present invention relates to an improvement in centrifugal analyzers of the type in which a disc is provided with a series of two loading wells for the sample to be analyzed and for the reagents respectively, and a reading chamber, or measuring cuvette, disposed radially, the measuring cuvette being in the path of an electromagnetic beam and an electromagnetic detector for transmitting the measurement signals to an electronic processing device. A transfer channel, provided with obstacles designed to insure the homogenization of the mixture of sample and reagent, is provided between the loding wells and the measuring cuvette.

According to one embodiment of the invention, the obstacles are preferably formed by chokes separating a series of wells, the bottom of which have a variable slope. According to another embodiment, the obstacles are formed by spikes extending into the transfer channel, which are disposed in a staggered pattern, or face to face, in the opening in the channel.

In still a third embodiment, the obstacles also include a threaded rod inserted into the opening of the channel in such a way as to insure an eddy flow in the pitch of the threaded rod and enzymes are immobilized on the threaded rod.

Also, in accordance with the invention, the measurement signals are peak signals corresponding to the center of the measuring cuvette. These peak signals are stored in an auxiliary memory for subsequent transfer to the electronic processing unit. Provision is also made so that the angle of incidence of the electromagnetic beam can vary during the course of the analysis.

The characteristics of the present invention will appear more clearly from the description given by way of example and made in reference to the accompanying drawings in which.

Figure 1:
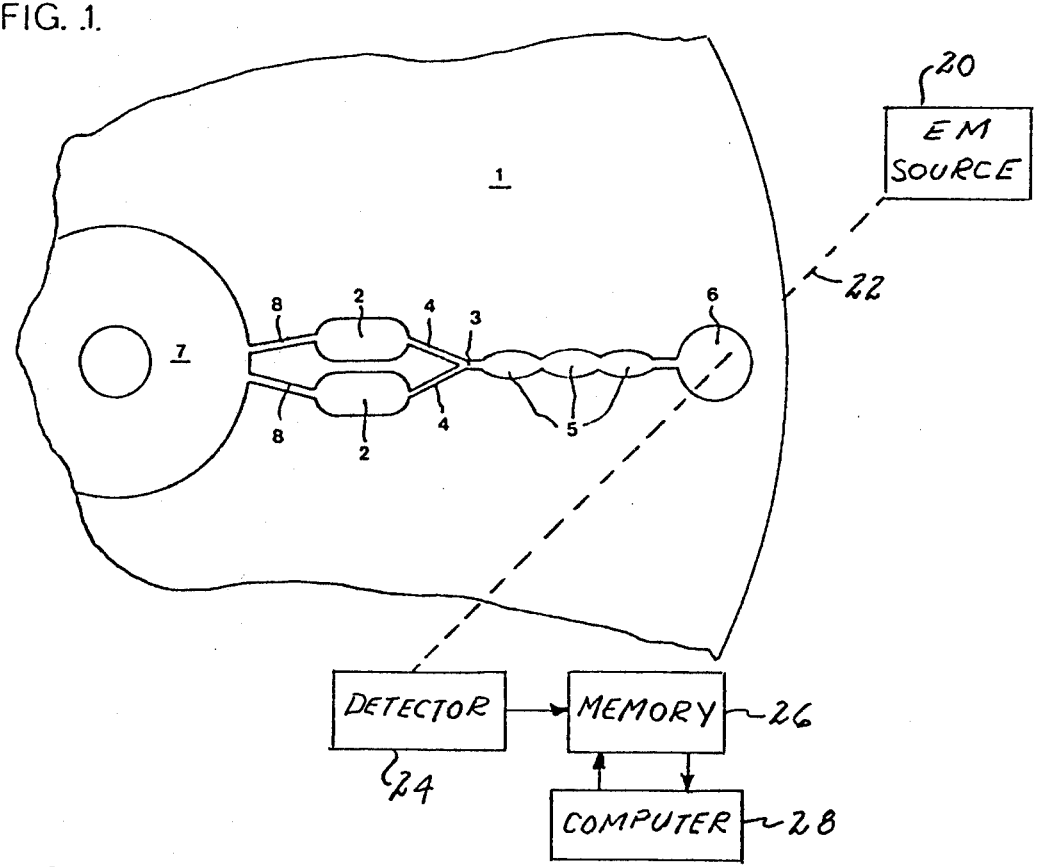
FIG. 1 is a plan view, partly in cross-section, of a disc according to one embodiment of the present invention in which the transfer channel is a series of chokes separating a series of chambers.

FIG. 1 shows a disc 1 with two loading wells 2 connected together and to the transfer channel 3 by two identical channels 4. Transfer channel 3 widens out to form cells 5 and empties into a measuring chamber 6. Loading wells 2 are each connected to the outside medium 7 through a channel 8.

Figure 2:
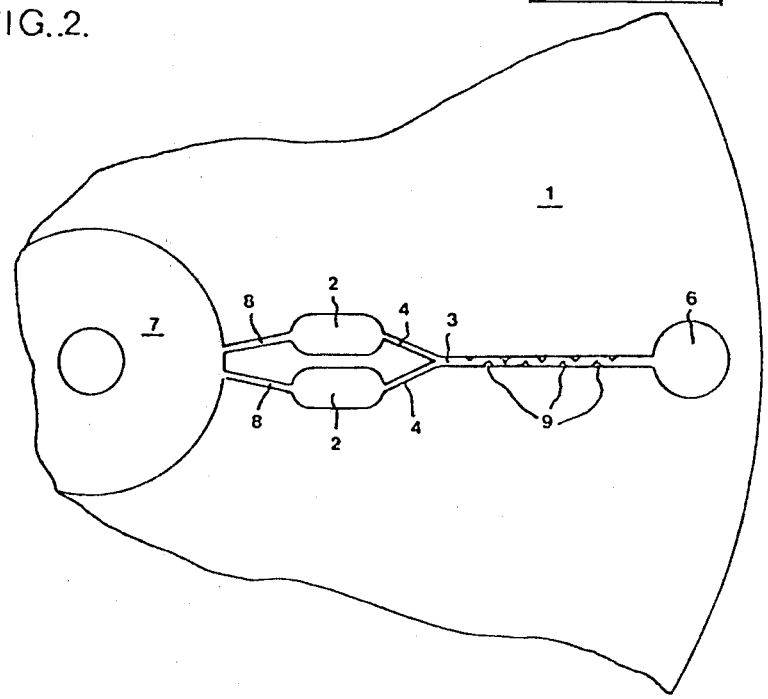
FIG. 2 is a plan view, partly in cross-section, of a disc according to one embodiment of the present invention in which the obstacles are formed by spikes projecting into the transfer channel.

FIG. 2 shows a disc 1 having two loading wells 2 connected together and to transfer channel 3 by two identical channels 4. Transfer channel 3 has spikes 9 projecting into the opening of this channel.

Figure 3:
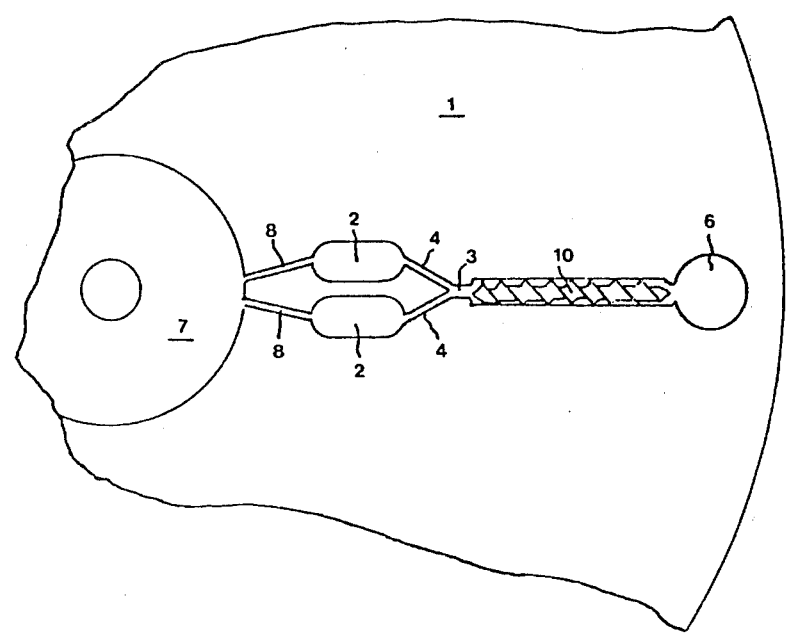
FIG. 3 is a plan view, partly in cross-section, of a disc according to one embodiment of the present invention in which the obstacles are formed by a threaded rod inserted in the channel.

FIG. 3 shows a disc 1 with two loading wells 2 connected together and to transfer channel 3 by two identical channels 4. A threaded rod 10 is inserted in the opening of transfer channel 3.

During use, the sample and the reagent are introduced respectively into wells 2 when disc 1 is stopped. When the disc begins to rotate, the liquids are moved into transfer channel 3 by means of channels 4 due to centrifugal force. In the embodiment of FIG. 1, the variation in the cross-section of transfer channel 3 produces pressure differences such that the mixture is homogeneous when it reaches the reading measuring chamber 6.

In the embodiment of FIG. 2, the presence of the spikes 9 projecting into the opening of transfer channel 3 produces pressure variations and an eddy flow such that the mixture is homogeneous when it reaches chamber 6.

In the embodiment of FIG. 3, the insertion of a threaded rod 10 into the opening of the transfer channel gives rise to an eddy flow when the liquids move in the pitch of the threaded rod, such that the mixture is homogeneous when it reaches the measuring chamber 6.

Enzymes are immobilized on the walls of threaded rod 10 in such a way that, as the reaction mixture sweeps over these walls, a heterogeneous catalytic reaction is produced. These enzymes, which do not form part of the reaction mixture, can be used for a fresh series of analyses. In goes without saying that, on the threaded rods inserted in the transfer channels, enzymes of a different kind can be immobilized.

The enzymatic reactions take place at very high speeds. The enzymatic reaction can be broken down into three phases, namely, a first rapid phase (generally less than a second) called pre-stationary, a second phase, generally occurring between one and several minutes, during which the concentration of the complex between the enzyme and the substrate is constant, and finally a third phase in which, before reaching equilibrium, the reaction follows a kinetics of an order greater than or equal to one.

Knowledge of the pre-stationary states and their properties is of great interest to the study of the mechanisms of functioning of the enzymes. At the present time, these pre-stationary states are studied by discrete devices designated by the term, "interrupted flux" devices which do not permit simultaneous analyses, under the same conditions, of the same sample under variable reaction conditions, or of different samples with the same reagent. The improvements imparted by the present invention make it possible to use the devices for analysis by centrifugation to study the kinetics and the properties of the reactions in the pre-stationary state. For example, in one embodiment of the present invention, during the passage from the rest state of the disc to a velocity of 2400 rpm, the transfer of the liquids into the measuring chamber 6 is obtained in a time not exceeding 30 ms, after which time, measurements are made at closely spaced intervals of time, for example, every 25 ms, for each of the measuring chambers located in the disc.

FIG. 1 illustrates a source 20 which produces a beam of energy 22 which is projected through the measuring chamber 6. The direction of impingement of the beam on the chamber 6 can be varied by varying the position of the source 20 and/or the disc 1, so that all parts of the chamber can receive the energy. Source 20 is of conventional construction and produces the wavelength(s) of energy needed.

A detector 24 is positioned on the other side of the disc 1 from the source 20 to receive the energy after it passes through chamber 6. The detector is constructed to detect the corresponding wavelength(s) of energy from source 20. It can be, for example, a photomultiplier. The position of the detector also can be varied.

The information produced by the detector 24 is applied to a memory 25. This memory is preferred to be separate from a computer, that is, it is effectively a part of, or adjunct to, the detector. The transfer of the information from memory 26 is controlled by a computer 28 which obtains and processes the stored information as needed. The foregoing arrangement of source, detector, memory and computer, also can used with the embodiments of FIGS. 2 and 3.

What is claimed is:
1. A rotor for a centrifugal analyzer comprising:

a generally disc shaped member defining therein;
a loading cell for a sample to be analyzed, said sample cell including an outlet,
a loading cell for a reagent, said reagent cell including an outlet,
a measuring chamber,
a common transfer channel having an inlet and an outlet, a separate communicating passage between the outlet of each said loading cell and said transfer channel inlet each of which passages passes the fluid from the respective cell to said transfer channel inlet without passing through the other cell, the outlet of said transfer channel transferring both the sample and the reagent to the measuring chamber, and
obstacle means in said transfer channel for mixing the sample and the reagent during the transfer.

2. A rotor as in claim 1 further comprising in combination:
means for transmitting electromagnetic energy to said measuring chamber,
means for detecting the electromagnetic energy after incidence on said measuring chamber and for producing an electrical signal representataive thereof, and
means for storing said signal.

3. The combination of claim 2 further comprising computer means for analyzing the signal produced by said detector means to provide data corresponding to the material in said measuring chamber.

4. A rotor as in claim 1 wherein said obstacle means comprise choke means separating said transfer channel into a series of chambers.

5. A rotor as in claim 4 wherein at least one of said chambers of said series of chambers has a wall with a variable slope.

6. A rotor as in claim 1 wherein said obstacle means comprise projections extending into said transfer channel.

7. A rotor as in claim 6 wherein said projections are disposed facing one another.

8. A rotor as in claim 6 wherein said projections are disposed in a staggered pattern.

9. A rotor as in claim 1 wherein said obstacle means comprise a threaded rod disposed in said channel.

10. A rotor as in claim 9 wherein said threaded rod is inserted in the channel to produce an eddy flow in the pitch of the rod.

11. A rotor for a centrifugal analyzer as in claim 1 further comprising means for producing electromagnetic energy which is transmitted to said measuring chamber.

12. The combination of claim 11 further comprising means for varying the angle of incidence of the energy with respect to said measuring chamber.

13. The combination of claim 11 further comprising means for detecting the energy passing through said measuring chamber, and means for storing the detected energy.

* * * * *